US007001985B2

(12) United States Patent
Nakamura

(10) Patent No.: US 7,001,985 B2
(45) Date of Patent: Feb. 21, 2006

(54) HUMAN CYCLIN I AND GENES ENCODING SAME

(75) Inventor: Takeshi Nakamura, Yokohama (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 1258 days.

(21) Appl. No.: 09/736,250

(22) Filed: Dec. 15, 2000

(65) Prior Publication Data

US 2005/0014139 A1 Jan. 20, 2005

Related U.S. Application Data

(60) Division of application No. 09/054,492, filed on Apr. 3, 1998, now Pat. No. 6,218,115, which is a continuation-in-part of application No. PCT/JP96/02905, filed on Oct. 7, 1996.

(30) Foreign Application Priority Data

Oct. 5, 1995 (JP) ............................................. 7-284663

(51) Int. Cl.
*C07K 14/435* (2006.01)

(52) U.S. Cl. ........................ 530/350; 530/350; 530/827
(58) Field of Classification Search ................ 530/350, 530/827

See application file for complete search history.

(56) References Cited

U.S. PATENT DOCUMENTS 5,247,070 A * 9/1993 Yamada et al. ............. 530/351
5,798,257 A * 8/1998 Zain et al. ................ 435/252.3

FOREIGN PATENT DOCUMENTS

WO    94/09135      * 4/1994
WO    PCT96/02905   * 10/1996

OTHER PUBLICATIONS

No reference cited.*
Nakamura T. et al. "Cyclin I: A New Cyclin Encoded by a Gene Isolated from Human Brain" Exp. Cell. Res. (Dec. 1995) vol. 221, No. 2, pp. 534–542.*
Robert P.F. et al. "A Novel Cyclin Associates with M015/CDK7 to Form the CDK–Activating Kinase" Cell (1994) vol. 78, pp. 713–724.*

Jonathon P. et al. Isolation of a Human Cyclin cDNA: Evidence for Cyclin mRNA and Protein Regulation in the Cell Cycle and for Interaction with p34$^{cdc2}$ Cell (1989), vol. 58, pp. 833–846.*

Tony Hunter et al., "Cyclins and Cancer", The Salk Institute, Cell, vol. 66, pp. 1071–1074, Sep. 20, 1991.*

John Lew et al., "Neuronal cdc2–like Kinase", TIBS 20, Reviews, Elsevier Science Ltd., pp. 33–37, Jan. 1995.*

Tony Hunter et al., "Cyclins and Cancer II: Cyclin D and CDK Inhibitors Come of Age", The Salk Institute, Cell, vol. 79, pp. 573–582, Nov. 18, 1994.*

Tamura et al., "Cyclin G: A New Mammalian Cyclin with Homology to Fission Yeast Cig 1", Research Institute for Microbial Diseases, Oncogene (1993), 8, pp. 2113–2118.

Hiroshi Matsushime, "Interaction Between Cyclins and cdks", Experimental Medicine, vol. 13, No. 6 (special number) 1995, pp. 1–2.

Masahiko Ohtsuki, "Signal Transfer Factor in Focus (Intranuclear Factor Highlight 10)", Experimental medicine, vol. 12, No. 16, (Nov.) 1994, pp. 1–2.

Daniel J. Lew et al., "Isolation of Three Novel Human Cyclins by Rescue of G1 Cyclin (CIn) Function in Yeast", The Scripps Research Institute, Cell, vol. 66, pp. 1197–1206, Sep. 20, 1991.

* cited by examiner

*Primary Examiner*—Karen A. Canella
*Assistant Examiner*—Lei Yao
(74) *Attorney, Agent, or Firm*—McDermott Will & Emery LLP

(57) ABSTRACT

This invention relates to a novel protein having a high degree of homology to the amino acid sequence of the so-called cyclin box which is characteristic of cyclins: they are herein referred to as "human cyclin I" or "human cyclin I protein." Further, the invention relates to a gene encoding their amino acid sequences and the protein: the gene is referred to as "gene encoding human cyclin I" or "human cyclin I gene." Also, the invention relates to expression vector into which the human cyclin I gene is incorporated as well as to a transformant into which the vector is introduced. Still further, the invention relates to a recombinant protein obtained by growing the transformant. In addition, the invention relates to a novel neuron-marking method using an anitisense nucleotide of the gene as probe. Furthermore, the invention relates to method for screening cancer cell using the human cyclin I gene.

1 Claim, 6 Drawing Sheets

Fig.1

```
                                                    GGAGGAGG    -61
AGGAAGAGGAGGAGAAGGTAGCTACAGCAAGCTGGGTAGCAGGCAGATCCAAAGGATATC    -1
ATGAAGTTTCCAGGGCCTTTGGAAAACCAGAGATTGTCTTTCCTGTTGGAAAAGGCAATC    60
 M  K  F  P  G  P  L  E  N  Q  R  L  S  F  L  L  E  K  A  I
ACTAGGGAAGCACAGATGTGGAAAGTGAATGTGCGGAAAATGCCTTCAAATCAGAATGTT   120
 T  R  E  A  Q  M  W  K  V  N  V  R  K  M  P  S  N  Q  N  V
TCTCCATCCCAGAGAGATGAAGTAATTCAATGGCTGGCCAAACTCAAGTACCAATTCAAC   180
 S  P  S  Q  R  D  E  V  I  Q  W  L  A  K  L  K  Y  Q  F  N
CTTTACCCAGAAACATTTGCTCTGGCTAGCAGTCTTTTGGATAGGTTTTTAGCTACCGTA   240
 L  Y  P  E  T  F  A  L  A  S  S  L  L  D  R  F  L  A  T  V
AAGGCTCATCCAAAATACTTGAGTTGTATTGCAATCAGCTGTTTTTTCCTAGCTGCCAAG   300
 K  A  H  P  K  Y  L  S  C  I  A  I  S  C  F  F  L  A  A  K
ACTGTTGAGGAAGATGAGAGAATTCCAGTACTAAAGGTATTGGCAAGAGACAGTTTCTGT   360
 T  V  E  E  D  E  R  I  P  V  L  K  V  L  A  R  D  S  F  C
GGATGTTCCTCATCTGAAATTTTGAGAATGGAGAGAATTATTCTGGATAAGTTGAATTGG   420
 G  C  S  S  S  E  I  L  R  M  E  R  I  I  L  D  K  L  N  W
GATCTTCACACAGCCACACCATTGGATTTTCTTCATATTTTCCATGCCATTGCAGTGTCA   480
 D  L  H  T  A  T  P  L  D  F  L  H  I  F  H  A  I  A  V  S
ACTAGGCCTCAGTTACTTTTCAGTTTGCCCAAATTGAGCCCATCTCAACATTTGGCAGTC   540
 T  R  P  Q  L  L  F  S  L  P  K  L  S  P  S  Q  H  L  A  V
CTTACCAAGCAACTACTTCACTGTATGGCCTGCAACCAACTTCTGCAATTCAGAGGATCC   600
 L  T  K  Q  L  L  H  C  M  A  C  N  Q  L  L  Q  F  R  G  S
ATGCTTGCTCTGGCCATGGTTAGTCTGGAAATGGAGAAACTCATTCCTGATTGGCTTTCT   660
 M  L  A  L  A  M  V  S  L  E  M  E  K  L  I  P  D  W  L  S
CTTACAATTGAACTGCTTCAGAAAGCACAGATGGATAGCTCCCAGTTGATCCATTGTCGG   720
 L  T  I  E  L  L  Q  K  A  Q  M  D  S  S  Q  L  I  H  C  R
GAGCTTGTGGCACATCACCTTTCTACTCTGCAGTCTTCCCTGCCTCTGAATTCCGTTTAT   780
 E  L  V  A  H  H  L  S  T  L  Q  S  S  L  P  L  N  S  V  Y
GTCTACCGTCCCCTCAAGCACACCCTGGTGACCTGTGACAAAGGAGTGTTCAGATTACAT   840
 V  Y  R  P  L  K  H  T  L  V  T  C  D  K  G  V  F  R  L  H
CCCTCCTCTGTCCCAGGCCCAGACTTCTCCAAGGACAACAGCAAGCCAGAAGTGCCAGTC   900
 P  S  S  V  P  G  P  D  F  S  K  D  N  S  K  P  E  V  P  V
AGAGGTACAGCAGCCTTTTACCATCATCTCCCAGCTGCCAGTGGGTGCAAGCAGACCTCT   960
 R  G  T  A  A  F  Y  H  H  L  P  A  A  S  G  C  K  Q  T  S
ACTAAACGCAAAGTAGAGGAAATGGAAGTGGATGACTTCTATGATGGAATCAAACGGCTC  1020
 T  K  R  K  V  E  E  M  E  V  D  D  F  Y  D  G  I  K  R  L
TATAATGAAGATAATGTCTCAGAAAATGTGGGTTCTGTGTGTGGCACTGATTTATCAAGA  1080
 Y  N  E  D  N  V  S  E  N  V  G  S  V  C  G  T  D  L  S  R
CAAGAGGGACATGCTTCCCCTTGTCCACCTTTGCAGCCTGTTTCTGTCATGTAGTTTCAA  1140
 Q  E  G  H  A  S  P  C  P  P  L  Q  P  V  S  V  M  *
CAAGTGCTACCTTTGAGTGTAAACTAAGGTAGACTACTTTGGGAATGAGAACATCCAAAA  1200
TCAGGAAAGGCTGTAGAAGGAAATATACCTTAACAGGCTGATTTGGAGTGACCCAGAAAA  1260
```

Fig.2A

```
CYCLIN A    ----MRAI-LVDWIVEVGEEYKL--QNETLHLAVNY    238
CYCLIN B    ----MRAI-LLDWLVQVQMKFRL--LQETMYMTVSI    229
CYCLIN C    ----LQIF-FTNVIQALGEHLKE--RQQVIATATVY     88
CYCLIN D    ----MRKI-VATVMLEVCEEQKC--EEVFPLAMNY      84
CYCLIN E    ----MRAI-LLDWLMEVCEVYKL--HRETFYLAQDF    157
CYCLIN F    ----MRYI-LLDWLVEVATMKDF--TSLCLHTVEC    337
CYCLIN G    MTARLRDFEVKDLLSLTQF-FGF--DTETFSLAVNL     33
CYCLIN H    ----LCKY-YEKRLLEFCSVFKPAMPRSVVGTACMY     86
CYCLIN I    VSPSQRD-FVIQWLAKLKYQFNL--YPETEALASSL     72

CYCLIN A    IDRFLSSM-SVLRGKLQLVGTAAMLLASK--FEE    269
CYCLIN B    IDRFMQNN-CVPKKMLQLVGVTAMFIASK--YEE    260
CYCLIN C    FKRFYARY-SLKSIDPVLMAPTCVFLASK--VEE    119
CYCLIN D    LDRFLSLE-PVKKSRLQLLGATCMFVASK--MKE    115
CYCLIN E    FDRYMATQENVVKTLQLIGISSLFIAAK--LEE    189
CYCLIN F    VDRYLRRR-LVPRYRLQLLGIACMVICTR--FIS    368
CYCLIN G    IDRFLSKMKVQAK-HLGCVGLSCEYLAVKSIEE     66
CYCLIN H    FKRFYLNN-SVMEYHPRIIMLTCAFLACK--VDE    117
CYCLIN I    LDRFLATVKAHEK-YLSCIAISCFFLAAKTVEED    105

CYCLIN A    IYPPEVAEFVYI-TDDTYTK------KQVL-RME    295
CYCLIN B    MYPPEIGDFAFV-TDNTYTK------HQIR-QME    286
CYCLIN C    FGVVSNTRIIAAATSVLKTRFSYAFPKFPYRMN    153
CYCLIN D    TIPLTAEKLCIY-TDNSIRP------EELL-QME    141
CYCLIN E    IYPEKLHQFAYV-TDGACSG------DEIL-TME    215
CYCLIN F    KELLTIREAVWL-TDNTYKY------EDLVRMM    394
CYCLIN G    RNVPLATDLIRI-SQYRFTV------SD-IMRME     92
CYCLIN H    FN-VSSP--------QFVGNLRESPLGQEKALE    141
CYCLIN I    ERLPVLKVLARD-SFCGCSS------SFAI-RME    131
```

Fig.2B

```
CYCLIN G:                                                    M TARLDFVK    11
CYCLIN I:  MKFPGPLENQ  RLSFLLEKAI  TREAQMWKVN  VRKMPSNQNV  SPSQRD-EVI   49

CYCLIN G:  DLSLTQF-E   GFDTESSEA   VNLLDFELSK  MEVQAKHLGE  VGLSCEYLAV   60
CYCLIN I:  QWLAKLKYQE  NLYPETFALA  SSLLDREFAT  VKAHPEYLSC  IAISCFFLAA   99

CYCLIN G:  LSIEKERNVE  LATDLLLIEQ  YRFTVED-LM  FMEKLVLEKV  CKVKATTAF   109
CYCLIN I:  KTVEBDERIE  VLKVLARDEF  CGCSSSEIE-  RHERELEDKL  NEDLHTAEPL  148

CYCLIN G:  QFEQLYYSLI  RELE-----   FBR-RNDLNF  ERLEAGLKAQ  -HCRIIFSKA  153
CYCLIN I:  DEEHIFHAIA  VSEREQLLFS  LPKLSPSQHL  AVETKELLHC  MACNQLL-QF  197

CYCLIN G:  KPEVLALAII  ALEIQALKYV  BETEGVECIQ  EHSKISGRDE  TFWQELVSKC  203
CYCLIN I:  RGEMLALAMV  SEEMEKLIPD  WESLTIELLQ  K-AQMDSSQE  IHCRELVAHH  246

CYCLIN G:  ETEYSSNKC-  -EKPNGQKEK  WIVSGRTARQ  LKHSYYRITH  LPTIPETMG   250
CYCLIN I:  ESTLQSSLPL  NEVYVYRPEK  HTLVTCDKGV  FRLHPSSVPG  PDFSKDNSKP  296

CYCLIN I:  EVPVRGTAAF  YHHLPAASGC  KQTSTKRKVE  EMEVDDFYDG  IKRLYNEDNV  346

CYCLIN I:  SENVGSVCGT  DLSRQEGHAS  PCPPLQPVSV  M                       377
```

HUMAN CYCLIN I AND GENES ENCODING SAME

This is a division of application Ser. No. 09/054,492, filed Apr. 3, 1998 now U.S. Pat. No. 6,218,115, which is a C-I-P of PCT/JP96/02905 filed Oct. 7, 1996.

TECHNICAL FIELD

This invention relates to human cyclin I gene. More specifically, it relates to the amino acid sequence for human cyclin I and a polynucleotide encoding the human cyclin I.

BACKGROUND ART

Cyclin is a general term to describe polypeptides that are subunits controlling the activities of cyclin-dependant protein kinase (Cdk) and eight species of cyclin, namely cyclins A–H, have been documented. Cyclin is known to form a complex with Cdk and to exhibit the capability of intracelluar phosphorylation.

Also, structural characteristics common in cyclins are that they passes a region called "cyclin box" which comprises about 100 amino acids within portions of their amino acid sequences. It is recognized that the eight species of cyclins hitherto known are provided with a high degree of homology in the amino acid sequences of this cyclin box. Hence, this cyclin box portion is believed to be a step necessary for binding to Cdk and controlling Cdk.

Furthermore, it is also recognized that the ability of cyclins to phosphorylate Cdk plays a critical role in the control of cell proliferation and through their ability cyclins bear close relation to phenomena such as cancer and immunity. Also, it is suggested that some cyclins are widely involved not only in the control of cell cycle, but also in the signal transmission.

Accordingly, there is strong likelihood that proteins having a high degree of homology in the amino acid sequence for the region called "cyclin box" as described above are cyclins. In this case, it is therefore anticipated that the proteins have the binding ability to Cdk and further that they have the ability to control kinase. See, Experimental Medicine, vol. 13, No. 6 (special issue), 1995.

DISCLOSURE OF INVENTION

The discovery and identification of novel protein having a high degree of homology to the amino acid sequence for the cyclin box which is characteristic of cyclins enables their use in elucidation of the detailed control mechanism of Cdk by cyclins as well as in the control of cell proliferation among others on the basis of the finding thus obtained. Further, it is thought that the elucidation of such protein with regard to variation of its quantity, its localization, its activation or the like within the cells brings knowledge useful to develop effective methods for the treatment of cancer or immune disorders, therapeutic agents therefor, methods for its diagnosis, diagnostic agents therefor, etc.

It is one object of this invention to discover and identify a novel protein having a high degree of homology to the amino acid sequence for the cyclin box which is characteristic of cyclins. A further object of the invention is to determine the amino acid sequence of the protein and to characterize a gene encoding the protein.

Also, it is an object of the invention to provide an expression vector into which an aforementioned genes is incorporated, a transformant into which the expression vector is introduced, and a recombinant protein obtained by growing the transformants.

Also, it is an object of the invention to provide a novel neuron marker based on the protein.

Further, it is another object of the invention to provide a method for screening cancer cells using the gene.

BRIEF DESCRIPTION OF DRAWINGS

FIG. 1 shows the base sequence of human cyclin I gene and its corresponding deduced amino acid sequence of human cyclin I protein.

FIGS. 2A and 2B show a comparison between the amino acid sequence of human cyclin I and the amino acid sequences of other members of the cyclin family. FIG. 2A shows a comparison in the cyclin box (the blackened parts indicate consensus amino acids), and FIG. 2B shows a comparison between human cyclin I and rat cyclin G (the underlined parts indicate the cyclin box).

FIG. 3A shows the results obtained using SCG10, while FIG. 3B shows those obtained using cyclin I antisense cRNA as a probe. Here, the parts visible in black are where neurons are concentrated. In the hippocampi (CA1, CA3, and DG), byramidal cells and granulocytes (both neurons) are strongly stained. DG represents "dentate gyrus," CA3 "Cajail's area 3," CTX "frontal cortex," CA1 "Cajail's area 1," and CP "choroid plexus."

BEST MODE FOR CARRYING OUT THE INVENTION

Figure 3A:
FIGS. 3A and 3B are photographs illustrative of localization of human cyclin I mRNA in neuron as determined by the in situ hybridization method using a rat brain section with the aid of an antisense cRNA probe. Both FIG. 3A (as denoted A in the figure) and FIG. 3B (as denoted F in the figure) show a rat brain section centered at its hippocampus

As a result of thorough investigations with an aim to achieving the aforementioned objects, the present inventor has extensively screened a gene encoding a protein present in human brain cells and succeeded in isolating a gene encoding cyclin-like polypeptide which has an amino acid sequence with a high degree of homology to the amino acid sequence for the known cyclin box. This gene will be herein referred to as "human cyclin I gene" and the protein encoded by this gene referred to as "human cyclin I." Further, the present inventor has succeeded in producing the recombinant cyclin I protein in large quantities by incorporating the isolated human cyclin I gene into an expression vector and introducing the expression vector into *E. coli* cells and have thus accomplished the invention.

Still further, the present inventor has developed a novel, simple method for selectively detecting neuron by using the thus obtained human cyclin I and a gene thereof. Also, the present inventor has succeeded in preparing anti-human cyclin I sera directed against an antigen resulting from a portion or the whole of the human cyclin protein.

Furthermore, the present inventor has succeeded in discovering a method to screen cancer cells by using the gene.

More specifically, this invention provides a polypeptide capable of forming a complex with kinase and controlling the activity of the kinase, said peptide comprising within a molecule thereof, at least a part or the whole of the amino acid sequence set forth in SEQ ID No. 1 in SEQUENCE LISTING.

Further, the invention provides a polypeptide comprising within a molecule thereof, at least the amino acid sequence set forth in SEQ ID No. 1 in SEQUENCE LISTING.

Also, the invention provides a polypeptide capable of forming a complex with kinase and controlling the activity of the kinase, said peptide comprising within a molecule thereof, at least an amino acid sequence into which a part or the whole of the amino acid sequence set forth in SEQ ID No. 1 in SEQUENCE LISTING has varied or that which a part or the whole of the same amino acid sequence has been induced to vary into, or comprising at least the amino acid sequence set forth in SEQ ID NO:1 in SEQUENCE LISTING.

Also, the invention provides a sense polynucleotide encoding at least a part of a polypeptide, said polypeptide comprising the amino acid sequence set forth in SEQ ID NO:1 in SEQUENCE LISTING.

Further, the invention provides a sense polynucleotide encoding one of the following peptides capable of forming a complex with kinase and controlling the activity of the kinase: (1) a polypeptide comprising within a molecule thereof, at least a part or the whole of the amino acid sequence set forth in SEQ ID NO:1 in SEQUENCE LISTING; (2) a polypeptide comprising within a molecule thereof, at least the amino acid sequence set forth in SEQ ID NO:1 in SEQUENCE LISTING; and (3) a polypeptide comprising within a molecule thereof, at least an amino acid sequence into which a part or the whole of the amino acid sequence set forth in SEQ ID NO:1 in SEQUENCE LISTING has varied or that which a part or the whole of the same amino acid has been induced to vary into.

Additionally, the invention provides an antisense polynucleotide corresponding to the sense polynucleotide encoding at least a part of a polypeptide, said polypeptide comprising the amino acid sequence set forth in SEQ ID NO:1 in SEQUENCE LISTING.

Further, the invention provides an antisense polynucleotide corresponding to the sense polynucleotide encoding at least a part of a polypeptide which comprises the amino acid sequence set forth in SEQ ID NO:1 in SEQUENCE LISTING, said antisense polynucleotide being capable of controlling the biosynthesis of one of the following polypeptides capable of forming a complex with kinase and controlling the activity of kinase: (1) a polypeptide comprising within a molecule thereof, at least a part or the whole of the amino acid sequence set forth in SEQ ID NO:1 in SEQUENCE LISTING; (2) a polypeptide comprising within a molecule thereof, at least the amino acid sequence set forth in SEQ ID No. 1 in SEQUENCE LISTING; and (3) a polypeptide comprising within a molecule thereof, at least an amino acid sequence into which a part or the whole of the amino acid sequence set forth in SEQ ID No. 1 in SEQUENCE LISTING has varied or that which a part or the whole of the same amino acid sequence has been induced to vary into.

Also, the invention provides double-strand polynucleotide comprising a sense polynucleotide encoding at least a part of a polypeptide which comprises the amino acid sequence set forth in SEQ ID NO:1 in SEQUENCE LISTING, together with an antisense polynucleotide corresponding to said sense polynucleotide.

In addition, the invention provides a method for detecting neuron comprising detecting mRNA which is present in said neuron and which contains a region encoding a polypeptide comprising the amino acid sequence set forth in SEQ ID NO:1 in SEQUENCE LISTING by means of a labeled nucleotide capable of hybridizing with said mRNA.

Furthermore, the invention provides an antibody directed against an antigen having a part or the whole of the polypeptide set forth in SEQ ID NO:1 in SEQUENCE LISTING, said antibody recognizing the polypeptide set forth in SEQ ID NO:1 in SEQUENCE LISTING or one of the polypeptides (1), (2), (3) as described above capable of forming a complex with kinase and controlling the activity of the kinase.

Also, the invention provides a recombinat plasmid comprising a double-strand polynucleotide which comprises a sense polynucleotide encoding one of the polynucleotides (1), (2), (3) as described above capable of forming a complex with kinase and controlling the activity of the kinase, together with an antisense polynucleotide of said sense polynucleotide.

In addition, the invention provides a recombinant microbial cell transformed with the aforementioned plasmid.

Furthermore, the invention provides a method for screening cancer cells using the cyclin I gene according to the invention.

(Samples for Identification of Human Cyclin I)

The types of cells from which the human cyclin I according to this invention is derived for its identification, or isolation purposes may, although not particularly limited thereto, be skeletal muscle cells, cultured fibroblasts or the like and cells derived from human cerebrum are most preferably used in the invention.

Moreover, as to identification of human cyclin I it is possible to utilize various properties, in chemical structure or biochemical characteristics, which are generally known in cyclins and to use those as screening markers. Specifically, for this purpose cyclin's property of binding to specific Cdk can be used as a marker in a method such as the in vitro binding method (Matsu, Cell Engineering, 13, 528–533, 1994). Further, as it has been already documented, cyclin's property of complementing a yeast variant that has a deficiency in progression of its cell cycle can, for example, be used as a marker in the gene complement-screening method through introduction of genes (Lew et al., Cell, 6, 1197–1206, 1991). In this particular invention, whether or not a marker contains an amino acid sequence having a high degree of homology to the amino acid sequence referred to as "cyclin box" that is commonly found in the chemical structures of cyclins and is believed to play an important biochemical role can preferably be utilized to find a desirable marker for screening the cyclins. A variety of methods relying on the procedures comparing with cyclins known in the art (e.g., judging significant differences based on calculation of homology to an amino acid sequence) can further be used to determine whether or not a marker has the cyclin box-like amino acid sequence, and they are not particularly limited in the invention.

In addition, this invention places no particular limitation to the forms of samples for the aforementioned screening, and a usable method is to directly or indirectly identify and isolate polypeptides which posses the properties as described above employing the aforementioned properties and through suitable means: for example, it is the screening of an expression library by means of an antibody directed against the known cyclin box. Also, among others a method to screen and identify genes which encode the amino acid sequence from a suitable cDNA library is usable. In the invention, it is particularly preferred that a group of cDNAS selected from a suitable cDNA library through random sampling are taken as samples for screening.

(Construction Methods of cDNA Libraries)

In this invention, there is no particular limitation to selection of the aforementioned suitable library and cDNA libraries available from various commercial sources and the like may preferably be used. The human cerebrum cDNA library as described above is most preferably usable in the invention. Furthermore, a normalized cDNA library can preferably be used in the invention: This library is, for example, obtained by the method of Sasaki et al., DNA Research 1, 91–96, 1994 (the content of each cDNA normalized).

(Cloning of Human Cyclin I Gene cDNA)

In this invention, there is no particular limitation to the degree of cloning within the normalized human brain cDNA library thus obtained above. A suitable sampling method, such as random sampling, enables a part of the library to be selected. In the invention, about $1\times10^3$~$5\times10^3$ cDNA pieces may preferably be screened at a time, for example.

Further, there is no particular limitation to the techniques of obtaining plasmids during screening, and standard methods known in the art (e.g., Cell Engineering Experimental Protocol, Yamamoto et al. Ed., Shujun Publisher, 1991, pp 71–107) can be used. For example, enabling methods are a method to slice an insert by digestion with restriction enzymes followed by incorporating the insert into a plasmid vector with the aid of ligase, an in vivo excision method using a helper phage, etc. In this invention, a plasmid may most preferably be converted to its form according to the in vivo excision method using the helper phage (i.e., the method described in the Uni-ZAP XR Cloning Kit Instruction Manual available from Stratagene Inc.).

(Determination of Base Sequences)

While determination of the base sequence of the plasmid obtained above allows the selection of a gene encoding the cyclin box-like amino acid sequence as described above, whether to analyze a part or the whole of the insert is not particularly predetermined in this invention. According to the invention, it is possible to determine a base sequence with an appropriate length and then to select a suitable plasmid based on the results of the determination, which may be preferable. Namely, it is preferred in the invention that several base sequences at its 5'-end of the insert are determined, amino acid sequences to be encoded are predicted from the determined base sequences, and then a plasmid is selected based on the foregoing results. In this instance, preferably at least 200 bases are to be analyzed at its 5'-end of the insert. This order of base number will sufficiently permits the determination of homology to the cyclin box.

In this invention, there is no particular limitation to the method for determining the base sequence at its 5'-end of the plasmid thus selected (not particularly limited and a suitable number at random may be selected, for example) and methods known in the art can be used. For example, the method relying on Taq cycle-sequencing (Biotechniques, 7, 494–499, 1989) can most preferably be used.

Furthermore, there is no particular limitation to the method for comparing the amino acid sequence derived from the base sequence thus obtained with the cyclin proteins known already and a homology analysis according to standard methods is possible. For example, the homology analysis has been enabled by employing a commercial program (e.g., GENETYX program (Ver. 27, Software Development Co.)) and a protein data base (e.g., Protein Database (NBRF, Release 43)). As a result of this homology analysis, it will become possible to select those that have greater than 30% homology from a series of 100 base sequences, for example.

To thoroughly analyze the plasmid selected by the aforementioned method a clone containing the whole region that encodes the protein should preferably be prepared. Screening methods to be used for this purpose are not limited in this invention, but it is particularly preferred that the information on the base sequence at the 5'-end obtained as described above is utilized. There is no limitation as to whether a part or the whole of the base sequence is utilized in this screening, but it is enough to be possible utilizing this base sequence for the screening. For example, although it is preferred to utilize a base sequence approximately corresponding to a half of the base sequence obtained as described above, that also depends on the screening method to be used.

As to the screening method, a variety of methods known in the art can preferably be used and they are not particularly limited. Specifically, the most preferred usable methods are a hybridization method using a labeled oligonucleotide, a RACE method using a primer along the 5'- or 3'-direction, etc. In this invention, it is particularly preferred that a labeled oligonucleotide having a base sequence which corresponds to about a half of the base sequence obtained as described above is used as a probe to perform screening through hybridization. There is no particular limitation to the aforementioned label and, for example, $[\alpha-^{32}P]$ dCPT, digoxigenin and the like can preferably be used. In addition, among others the hybridization conditions are not particularly limited and a variety of conditions previously known in the art can preferably be used in the invention (e.g., Cell Engineering Experimental Protocol, Yamamoto et al. Ed., Shujun Publisher, 1991, pp. 57–65).

In this invention, there is no particular limitation to the methods for determining the base sequence of the insert from a positive clone screened as described above and a variety of methods known in the art are usable. For example, it is possible to use the method where deficient variants are prepared, the base sequences of individual clones determined, and on that basis ligation is achieved.

A variety of methods known in the art as has been described already can be used to determine the base sequence of the longest insert among the inserts obtained as described above and, for example, one of them is a method where sequence primers are successively prepared from segments the amino acid sequences of which have been determined and they are read.

(The Determined Human Cyclin I Gene Base Sequence)

The determined base sequence of a polynucleotide encoding the human cyclin I polypeptide is represented by SEQ ID NO:2 in SEQUENCE LISTING.

The aforementioned polynucleotides according to this invention encompass a polynucleotide comprising a base sequence which is the base sequence represented by SEQ ID NO:2 in SEQUENCE LISTING and having no ATG bonded at its 5'-end.

The polynucleotides of the invention also encompass DNA including 5'-flanking polynucleotides.

Also, it is possible to vary a part of the structures of polynucleotides and deduced polypeptides therefrom without altering their principal activities (e.g., to activate phosphorylation) by means of natural or artificial mutation.

Consequently, the polynucleotides according to the invention can possibly include base sequences encoding polypeptides which have structures of analogous isomers, variants or mutants of all the polypeptides as described above.

Furthermore, it is possible to substitute at least one base of the base sequence of a polynucleotide with other kinds of bases without altering the amino acid sequence of a polypeptide produced by the polynucleotide in accordance with degeneracy in genetic codes. Hence, the polynucleotides of this invention can also possibly contain the base sequences converted by substitutions based on the degeneracy in genetic codes. In this case, the amino acid sequence deduced from the base sequence which has been obtained by the aforementioned substitution accords with the amino acid sequence set forth in SEQ ID NO:1 in SEQUENCE LISTING as previously defined.

(The Amino Acid Sequence of Human Cyclin I)

SEQ ID NO:1 in SEQUENCE LISTING represents the amino acid sequence of the human cyclin I polypeptide which is presumed based on the polynucleotide encoding the human cyclin I polypeptide the amino acid sequence of which has been determined according to the methods as explained above.

The amino acid sequences according to this invention encompass a polypeptide which is derived from the aforementioned amino acid sequence having no methionine bonded at its N-terminal.

Also, it is possible to vary a part of the structure of polynucleotides encoding polypeptides without altering their principal activities by means of natural or artificial mutation (e.g., Molecular Cloning, A Laboratory Manual, $2^{nd}$ ed., Cold Spring Harbor Laboratory Press, 15.1–15.113, 1989) and the human cyclin I polypeptides according to the invention encompass polypeptides which have structures corresponding to, analogous isomers, variants or mutants with the amino acid sequences as described above.

(The Characteristics of Cyclin)

As shown in FIG. 2, the amino acid sequence translated from the determined base sequence displays significant homology to members of the already known cyclin family with respect to their cyclin boxes. Particularly, 41% homology is observed against rat cyclin G (Tamura et al., Oncogene, 8, 2113–2118, 1993) and 36% homology also observed against human cyclin E. Since the known cyclin members are referred to as "icyclins A~H" in the order of their identification, this novel cyclin will be referred to as "cyclin I." As shown in FIG. 2, cyclin I identified in the invention displays significant homology to other members of the cyclin family within the region of cyclin boxes.

By analogy to biological functions of the known members, it is expected that the cyclin I protein identified in this invention is able to bind to specific members of cdks which are kinds of kinase through its cyclin box and has the function of activating the kinase. Furthermore, according to conventional techniques known in the art such as antisense, it is possible to find a means to effectively inhibit synthesis of the human cyclin I protein and to provide a method for treating diseases in which the aforementioned kinase enzymes play an important role.

(Transformed *E. Coli* Containing Cyclin I)

Following the PCR method (Michael A. Innis et al. Ed., T. Saito Rev., PCR Experimental Manual, HBJ Press, 1991), only the region encoding proteins can be amplified from the clone obtained as described above which has the longest insert cDNA (about 1.7 kb insert), and can be inserted into the EcoRI site of PCRII plasmid (Invitrogen Inc.). Although in this case the primers to be used are not particularly limited in the invention, the primers which are described in the following and which have the base sequences set forth in SEQ ID Nos. 3 and 4 in SEQUENCE LISTING are most preferably usable:

(ORF-s)    CGTTCCCGGGTATGAAGTTTCCAGGGCCTTTGG; and (ORF-AS)   ACGGCTCGAGCTACATGACAGAAACAGGCTG Amplification under the known conditions (e.g., employing a DNA thermal cycler (Perkin Elmer Cetus Inc.) or the like) allows the region encoding proteins to be obtained. To insert this PCR fragment into a suitable plasmid such as the ECORI site of pCRII plasmid, known methods (e.g., employing a TA cloning kit (Invitrogen Inc.) and following its attached operating instructions) can be used.

According to the aforementioned procedures, it will be possible to obtain transformed *E. coli* containing plasmid pCRII-cyclin I and, if necessary, b this transformant will possibly be furnished from the strain originally deposited on Sep. 8, 1995 in the National Institute of Bioscience and Human-Technology, Agency of Industrial Science and Technology, Ministry of International Trade and Industry locating at 1–3 Higashi 1 chome, Tsukuba-shi, Ibaraki-ken 305, Japan accorded Accession No. FERM P-15166: the strain transferred on Sep. 3, 1996 to deposition under the terms of the Budapest Treaty in the National Institute of Bioscience and Human-Technology, Agency of Industrial Science and Technology, Ministry of International Trade and Industry locating at 1-3 Higashi 1 chome, Tsukuba-shi, Ibaraki-ken, 305 Japan accorded Accession No. FERM BP-5652.

(Large Scale Production of Recombinant Cyclin I Protein)

It is possible to insert into a suitable vector (e.g., between SmaI site and XhoI site within a pGEX-4T-1 vector (Pharmacia Inc.)), the PCR fragment comprising only the region that encodes the aforementioned cyclin I protein; to grow *E. coli* cells containing the resulting plasmid under standard conditions; then to induce expression of the recombinant cyclin I protein (e.g., by using IPTG (Sima Inc.))(in this case, the protein is formed as a protein fused with GST protein); and to recover the recombinant cyclin I protein from the cells. This procedure can be performed according to conventionally known methods such as a modification of the method described in the instruction manual of pGEX-4T-1 vector (Pharmacia Inc.). Thus, it has become possible to produce the cyclin I protein in large quantities.

(Cyclin I as Neuron Marker)

The present inventor has investigated as to which brain cells the cyclin I protein according to this invention is abundant in, and as a result, discovered that the protein is mostly localized in neuron. Based on this finding, the present inventor has found a method to specifically detect neuron by means of the cyclin I protein and the cyclin I gene according to the invention. An embodiment of the invention is described below.

For example, (1) a brain section sample in appropriate thickness is prepared using a cryostat (Hacker Instruments Inc.) and placed on a slide glass coated with zeratin; and then (2) the section is appropriately treated (e.g., postfixing, acetylation, and dehydration according to a modification of the method by Himi et al., Neuroscience, 60, 907–926, 1994); and hybridization is further performed using a probe labeled with a suitable labeling agent (e.g., digoxigenin).

An antisense probe of cyclin I is prepared by performing in vitro transcription with T3RNA polymerase (Biolabs Inc.)

in the presence of digoxigenin-labeled UTP (Boehringer Inc.) after digestion of the plasmid containing cyclin I cDNA with a suitable restriction enzyme that cleaves only the 5'-end of the cDNA followed by its ring-opening. Further, an antisense probe of SCG10 which is to be used as a positive control for the neuron marker is prepared in like manner; for example it is possible according to a modification of the method by Himi et al., as described in Neuroscience, 60, 907–926, 1994.

(3) In situ hybridization, RNAse treatment, and washing can be performed according to a method known in the art such as the method by Himi et al., Neuroscience, 60, 907–926, 1994. Subsequently, after the section is treated with a blocking agent (DIFCO Inc.), it is incubated with an anti-digoxigenin-alkaline phosphatase labeled antibody (Boehringer Inc.). Signals are detected by chromophoric visualization using NBT (nitroblue tetrazolium salt) and X-phosphate toluidium salt, both of which are available from Boehringer Inc.

Figure 3B:
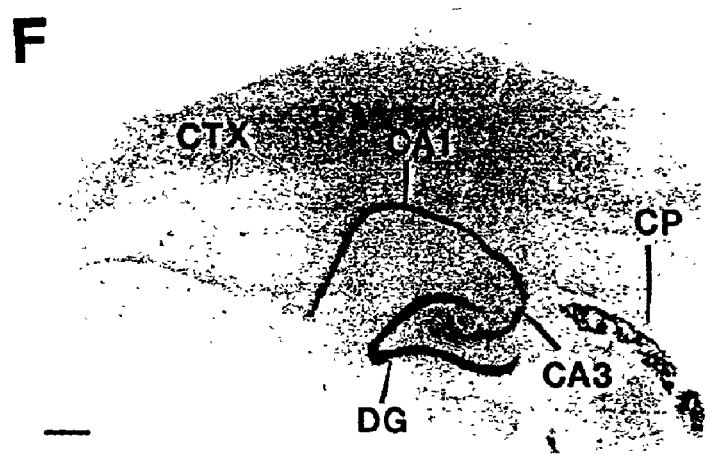

As the results are shown in FIG. 3, the hippocampus where neurons are concentrated gives clear signals. FIG. 3A shows the results obtained using the antisense probe of SCG10, while in FIG. 3B the cyclin I gene and a rat brain section neighboring on the hippocampus were used. Both FIG. 3A and FIG. 3B show clear signals at completely identical sites, where neurons are localized.

Consequently, any base sequence complementary to a partial or the whole base sequence of the cyclin I gene finds value as a neuron marker. For example, it can be utilized to find the sites of neuron in a brain section-during research or clinical investigations.

(Preparation of Anti-Cyclin I Antibodies and Method for the Detection of Cyclin I Protein)

The preparation of an antibody can be performed using a part or the whole of a peptide comprising the amino acid sequence set forth in SEQ ID No. 1 in SEQUENCE LISTING, or the purified cyclin I protein according to the method as described in "Antibodies; A Laboratory Manual" (Cold spring Harbor Laboratory Press, 1988). For example, procedures known in the art can be used to immunize rabbits and to provide antisera. Also, it is well recognized that if polyclonal antibodies having sufficient antibody titers can be produced by immunosensitization as the results from Example 6 show, monoclonal antibodies are produced by the use of hybridomas employing lymphocytes of the immunized animal. Accordingly, this invention encompasses monoclonal antibodies directed against the cyclin I protein.

According to western blotting employing the antibodies prepared as described above, detection and identification of the cyclin I protein has been enabled. Specifically, a sample containing the cyclin I protein is charged on an acrylamide gel and allowed to react with the aforementioned antisera, which enables the detection of a band at a 43 kDa position (which corresponds to the polypeptide having SEQ No. 1 in SEQUENCE LISTING). The foregoing manipulations can be performed according to conventional methods known in the art, such method as described in Chapter 12, "Antibodies; A Laboratory Manual" (Cold Spring Harbor Laboratory Press, 1988).

(Cyclin I as Proliferation Maker)

The present inventors have found that a probe derived from the cyclin I gene can be utilized for the purpose of determining that quiescent cells such as those in colon tissues pass into their proliferation state.

For example, RNAs are extracted from cancerous sections and their neighboring normal sections within excised colon cancer tissues, and analyzed by northern blotting where a nucleic acid sequence derived from the cyclin I gene labeled by a suitable means (e.g., radiolabeling with $^{32}P$) is used as a probe: The northern blotting analysis can, for example, be performed following the method as described in Cell Engineering Experimental Protocol, Shujun Publisher, pp. 149–150.

Figure 5:
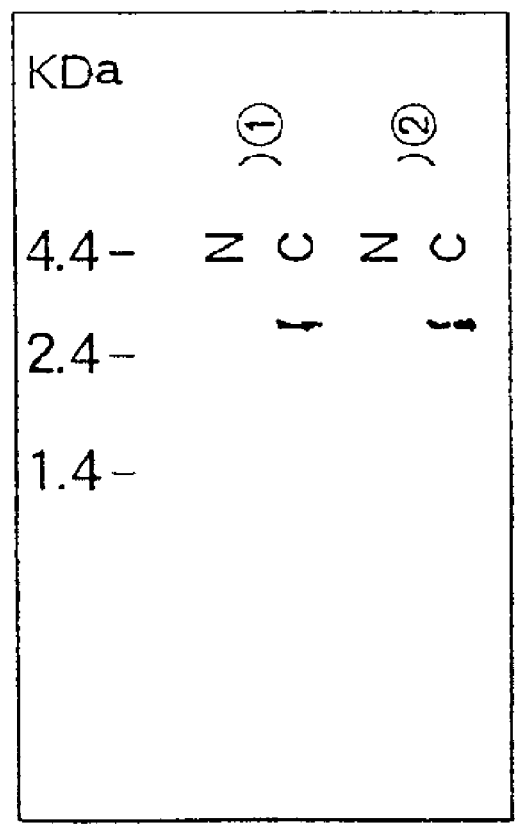
FIG. 5 shows increases in cyclin I mRNA in colon cancer tissues. In both specimens 1 and 2 the increases are observed in the cancerous sections (C) compared with the normal sections (N).

As the results are shown in FIG. 5, mRNA of cyclin I can hardly be detected, whereas its marked increase can be noted in the cancerous section.

Accordingly, a base sequence that is complementary to a partial or the whole base sequence of the cyclin I gene can be utilized for the purpose of determining that quiescent cells have passed into their proliferation state; namely, it can be used as a cancer marker such as that for colon cancer during research and clinical investigations.

(Control of the Biosynthesis of Cyclin I Protein by an Antisense Nucleotide)

An antisense nucleotide which are useful in this invention to control or inhibit the biosynthesis of cyclin I protein can be selected by means known in the art and, for example, that with desired structure is available through a chemical synthesis (e.g., Takeuchi et al., Experimental Medicine, 12, 1657–1663, 1994). Also, it can be provided by the method where an antisense segment is incorporated into a suitable vector such as pCMV1 and expressed in a cell; for example, it is possible according to a modification of the method by Kobayashi et al. as described in Antisense Research and Development, 5, 141–148, 1995.

Nucleotide sequences to be usable may be those which are the antisense segments of polynucleotides having a part or the whole of the base sequence set forth in SEQ ID No. 2 in SEQUENCE LISTING and also are polynucleotides capable of inhibiting the biosynthesis of the polypeptides as described below. Namely, they are polypeptides capable of forming a complex with kinase and controlling the activity of the kinase and may be one of the following polypeptides: (1) a polypeptide comprising within a molecule thereof, at least a part or the whole of the amino acid sequence set forth in SEQ ID No. 1 in SEQUENCE LISTING; (2) a polypeptide comprising within a molecule thereof, at least the amino acid sequence set forth in SEQ ID No. 1 in SEQUENCE LISTING; and (3) a polypeptide comprising within a molecule thereof, an amino acid sequence into which a part or the whole of the amino acid sequence set forth in SEQ ID No. 1 in SEQUENCE LISTING has varied or that which a part or the whole of the same amino acid has been induced to vary into.

For administration or incorporation to cells, in the case of an oligonucleotide it is enabled by the method by Takeuchi et al. as described in Experimental Medicine, 12, 1657–1663, 1994; in the case of use of an expression vector, it is enabled by the method by Kobayashi et al. as described in Antisense Research and Development, 5, 141–148, 1995.

Having controlled or inhibited the biosynthesis of the cyclin I protein intracellularly, the antisense nucleotides of the invention can be used in the following: (i) an effective reagent or method for analyzing intracellular physiological effects of cyclin I; or (ii) an effective reagent or method for studying influences which cyclin I, being excessively present within the cells, has on said cells, tissues, or a living body, in which case they are made applicable to therapeutic agent for removing or alleviating undesirable influences or the like caused by cyclin I's excessiveness.

The abbreviations used herein to describe the invention are tabulated below:

| Abbreviations | |
|---|---|
| DNA | Deoxyribonucleic acid |
| A | Adenine |
| C | Cytosine |
| G | Guanine |
| T | Thymine |
| Ala (A) | Alanine |
| Arg (R) | Arginine |
| Asn (N) | Asparagine |
| Asp (D) | Aspartic acid |
| Cys (C) | Cystine |
| Gln (Q) | Glutamine |
| Glu (E) | Glutamic acid |
| Gly (G) | Glycine |
| His (H) | Histidine |
| Ile (I) | Isoleucine |
| Leu (I) | Luecine |
| Lys (K) | Lysine |
| Met (M) | Methionine |
| Phe (F) | Phenylalanine |
| Pro (P) | Proline |
| Ser (S) | Serine |
| Thr (T) | Threonine |
| Trp (W) | Tryptophan |
| Tyr (Y) | Tyrosine |
| Val (V) | Valine |

EXAMPLES

Although this invention is concretely illustrated by way of examples, it is not limited to the following examples insofar as it does not depart from its essence.

Example 1

Construction of Human Brain-Derived Normalized cDNA Library

The normalized cDNA library was constructed using mRNA derived from a human cerebrum. According to the method of Sasaki, et al., DNA Research 1, 91–96, 1994, step (i)—selfhybridization in a semisolid system, step (ii)—construction of a phage cDNA library from the mRNA treated in step (i), and step (iii)—conversion of insert cDNA into cRNA were carried out in a sequence of (i)–(ii)–(iii)–(i)–(ii) and the normalized cDNA library was constructed.

Cloning of Human Cyclin I Gene cDNA (1) One hundred µL out of 1 mL of the normalized cDNA library constructed by the aforementioned method was converted into a plasmid form according to the in vivo excision method (as described in the Uni-Zap XR Cloning Kit Instruction Manual available from Stratagene Inc.) employing a helper phage (EXAssist available from Stratagene Inc.).

More specifically, 200 µL of E. coli XL-1 Blue, 100 µL of the normalized cDNA library, and 1 µL of helper phage R408 (>1×10⁶ pfu/ml) were mixed in a 50 mL test tube and the ZAP was allowed to be transfected by the helper phage at 37° C. for 15 minutes.

To the mixture was added 5 mL of a 2×YT medium (10 g NaCl, 10 g Bacto Yeast Extract, and 16 g Bactotryptone/1L) and it was incubated under shaking at 37° C. for 3 hours to have phagemid excreted from E. coli.

After heat-treatment at 70° C. for 20 minutes, the culture was centrifugated at 4000 g and the cells were destroyed. The supernatant phagemid was transferred to a different test tube.

This supernatant contained pBluescript SK(–) particles, and 200 µL of the supernatant or 20 µL of its 100 times dilution and 200 µL of XL-1 Blue (OD 600=1.0) were mixed at 37° C. for 15 minutes to induce transfection.

After plating 1~100 µL of the cultured solution on a LB/Amp plate, it was incubated overnight at 37° C. Colonies that appeared were E. coli (XL-1 Blue) transformants which had double-stranded pBluescript SK(–) containing insert DNA.

(2) A plasmid was prepared from the aforementioned E. Coli using a QIAwell 8 Plus kit (Qiagen Inc.).

(3) The base sequence at its 5'-end of the insert DNA of the thus obtained plasmid was determined on an autosequencer 373A (Perkin Elmer) using the Taq cycle-sequencing method (Biotechniques, 7, 494–499, 1989).

(4) The amino acid sequence obtained by translation of the thus determined base sequence was compared with a protein database (NBRF, Release 43) by use of the GENETYX Program (Ver. 27 available from Software Development Inc.) to carry out homology analysis.

(5) More than 500 plasmids were subjected to the sequence determination and homology analysis to select the one that had an amino acid sequence like the cyclin box (named FC6 where "FC" is the abbreviation of Forebrain Cortex). To analyze it further in detail, a clone containing the whole region that encodes the protein was prepared by the procedures described below.

(6) With cDNA library derived from temporal lobe cortex (Stratagene Inc.), screening was performed using the 5'-end half of the aforementioned FC6 clone as a probe.

Twenty µL of the phage library solution and 200 µL of E. coli XL-1 Blue were incubated at 37° C. for 15 minutes. This culture was added to 2~3 mL of top-agar (48° C.), the mixture was plated on six NZY agar plate, and was grown overnight at 37° C.

Approximately the number of 50,000 of plaque were cultured on a 100 mm square plate. Therefore, the number of ca. 3×10⁵ of plaque were cultured on 6 plates and used for screening.

The NZY plate was cooled at 4° C. for two hours and a nylon filter (High Bond N+; available from Amasham Inc.) was placed over the plate and allowed to stand for two minutes.

This filter was peeled off, dried on a filter paper, and the plaques were fixed under the ultraviolet irradiation to prepare a screening filter.

Hybridization was performed according to the procedures as described below.

The probe for use in hybridization was the one that had been obtained by labeling the 5'-end half of FC6 clone with ³²P-dCTP using a Megaprime Labeling Kit (Amasham Inc.).

A mixture of 5×SSC (NaCl 0.15 M, sodium citrate (pH 7.0) 0.015 M), 50% formamide 1×denhardt solution (bovine serum albumin (Fraction V) 0.2% poly(vinylpyrolidone) 0.2%, and Ficoll400 0.2%), 0.1% SDS, and 100 µg/mL of salmon sperm DNA was used as a prehybridization solution.

The filter was first incubated in the prehybridization solution at 42° C. for three hours, and then in a hybridization solution to which the labeled probe had been added, at 42° C. for 16 hours to effect hybridization.

Following the aforementioned manipulations, three positive clones were obtained. The centers of plaques of the resulting positive ZAP phage clones on the agar plates were scooped out with a Pasteur pipette and the clones were eluted in a mixed solution of 500 µL of SM buffer and 20 µL of chloroform, and were allowed to stand overnight after having been vortexed.

Two hundred µL of E. coli XL-1 Blue, 200 µL of the positive phage clone (>1×10⁵ pfu/ml phage particles), and one µL of helper phage R408 (>1×10⁶ pfu/ml) were mixed in a 50 mL test tube and the ZAP was allowed to be transfected by the helper phage at 37° C. for 15 minutes.

To the mixture was added 5 mL of the 2×YT medium (10 g NaCl, 10 g Bacto Yeast Extract, and 16 g Bactotryptone/ 1L) and it was incubated under shaking at 37° C. for 3 hours to have phagemid excreted from *E. coli*. After heat-treatment at 70° C. for 20 minutes, the culture was centrifuged at 4,000 g and the cells were destroyed. The supernatant phagemid was transferred to another test tube.

This supernatant contained pBluescript particles, and 200 µL of the supernatant or 20 µL of its 100 times dilution and 200 µL of XL-1 Blue (OD 600=1.0) were mixed at 37° C. for 15 minutes to induce transfection.

After plating 1~100 µL of the cultured solution on a LB/Amp plate, it was incubated overnight at 37° C. Colonies that appeared were *E. coli* (XL-1 Blue) transformants which had double-stranded pBluescript SK(-) containing insert DNA.

Plasmids were prepared from the three positive *E. coli* clones using a QIAprepPlasmid Kit (Qiagen Inc.) and among them, the clone that had the longest insert DNA (about 1.7 kb insert) was subjected to the DNA base sequencing as described below.

(7) The base sequence of the thus obtained 1.4 k clone was determined on an autosequencer 373A (Perkin Elmer) using the Taq cycle-sequencing method (Biotechniques, 7, 494–499, 1989). Based on the results of the cDNA base sequence analysis for the resulting human cyclin I, 1328 bases are shown in FIG. 1. The open reading frame of the human cyclin I is comprised of 1134 bases, which encode 377 amino acids.

Sequence Analysis of Amino Acids Encoded by Human Cyclin I Gene

As shown in FIG. 2, the amino acid sequence translated from the determined base sequence displays significant homology to members of the already known cyclin family with respect to their cyclin boxes. Particularly, 41% homology is observed against rat cyclin G (Tamura, et al., Oncogene, 8, 2113–2118, 1993) and 36% homology also observed against human cyclin E. Since the known cyclin members are referred to as "cyclins A~H" in the order of their identification, this novel cyclin will be referred to as "cyclin I." As shown in FIG. 2, cyclin I identified in the invention displays significant homology to other members of the cyclin family within the region of cyclin boxes.

Example 2

Following the PCR method (Michael A. Innis, et al., Ed., T. Saito Rev., PCR Experimental Manual, HBJ Press, 1991), only the region encoding proteins was amplified from the clone prepared according to Example 1 which had the longest insert cDNA (about 1.7 kb insert), and was inserted to the EcORI site of PCRII plasmid ( Invitrogen Inc.). The primers for use were as follows:

(ORF-s)   CGTTCCCGGGTATGAAGTTTCCAGGGCCTTTGG; and (ORF-AS)  ACGGCTCGAGCTACATGACAGAAACAGGCTG With the use of the primer concentrations of 20 pmol/µL and 0.025 U/µL of Taq DNA polymerase at three cycles, a DNA thermal cycler (Perkin Elmer (Cetus)Inc.) was employed to do amplification and to obtain the region that encodes the protein.

To insert this PCR fragment into the ECORI site of the PCRII plasmid, a TA cloning kit (Invitrogen Inc.) was employed following its attached operating instructions. Transformed *E. coli* containing plasmid pCRII-cyclin I prepared according to the method as described above was designated as pCRII-cyclin I and deposited on Sep. 8, 1995 in the National Institute of Bioscience and Human-Technology, Agency of Industrial Science and Technology, Ministry of International Trade and Industry locating at 1-3 Higashi 1 chome, Tsukuba-shi, Ibaraki-ken 305, Japan accorded Accession No. FERM P-15166. Further, it was transferred on Sep. 3, 1996 to deposition under the terms of the Budapest Treaty in the National Institute of Bioscience and Human-Technology, Agency of Industrial Science and Technology, Ministry of International Trade and Industry locating at 1–3 Higashi I chome, Tsukuba-shi, Ibaraki-ken 305, Japan accorded Accession No. FERM BP-5652.

Example 3

Investigation on Applicability of Cyclin I as Neuron Marker (1) Brain sections from adult male rats (Sprague-Dawley, three months old) in a thickness of 13 microns were prepared using a cryostat (Hacker Instruments Inc. ) and placed on slide glasses coated with zeratin.

(2) According to the method by Himi, et al., Neuroscience, 60, 907–926, 1994, the section was subjected to postfixing, acetylation, and dehydration and then hybridization was performed using a probe labeled with digoxigenin.

An antisense probe of cyclin I was prepared by performing the in vitro transcription with T3RNA polymerase (Biolabs Inc.) in the presence of digoxigenin-labeled UTP (Boehringer Inc.) after ring-opening of the aforementioned plasmid digesting the plasmid at XhoI. In like manner, an antisense probe of SCG10 which was to be used as a positive control for the neuron marker was prepared (Neuroscience, 60, 907–926, 1994).

(3) In situ hybridization, RNAse treatment, and washing were performed according to the method by Himi, et al., Neuroscience, 60, 907–926, 1994. Subsequently, the section was treated with a blocking agent (DIFCO Inc.) and thereafter, was incubated with an anti-digoxigenin-alkaline phosphatase labeled antibody (Boehringer Inc.). Signals were detected by chromophoric visualization using NBT (nitroblue tetrazolium salt) and X-phosphate toluidium salt, both of which were available from Boehringer Inc. FIG. 3 illustrates the results.

Here, the hippocampus where neurons are concentrated shows clear signals. FIG. 3 shows the results obtained using the antisense probe of SCG10, while in FIG. 3B a rat brain section neighboring on the hippocampus and cyclin I genes were used. Both FIG. 3A and FIG. 3B show clear signals at completely identical sites, where neurons are localized. Consequently, any base sequence complementary to a partial or the whole base sequence of the cyclin I gene finds value as a neuron marker. For example, it can be utilized to find the sites of neuron in a brain section during research or clinical investigations.

Example 4

Large Scale Production of Recombinant Cyclin Protein (1) The PCR fragment prepared according to Example 2 and which comprised only the region that encodes the protein was inserted between SmaI site and XhoI site within a pGEX-4T-1 vector (Pharmacia Inc.).

(2) *E. coli* cells containing the resulting plasmids were grown, then expression of the recombinant cyclin I protein was induced by IPTG (Sima Inc. ), in which case the protein was formed as a protein fused with GST protein, and the recombinant cyclin I protein was recovered from the cells.

The foregoing procedure was performed according to the method described in the instruction manual of pGEX-4T-1 vector (Pharmacia Inc.).

Example 5
Preparation of Anti-Cyclin I Antibodies (Part 1)

(1) The preparation of the antibodies was performed using the recombinant cyclin I protein prepared according to Example 4 by following a modification of the method as described in Chapter 5, "Antibodies; A Laboratory Manual" (Cold Spring Harbor Laboratory Press, 1988). These antibodies were used to immunize rats in order to obtain antisera.

(2) A solution extracted from TIG-1 cells containing the cyclin I protein was charged on an acrylamide gel and subjected to analysis by western blotting using the antiserum prepared according to Procedure (1), which detected a band corresponding to the cyclin I protein at a 43 kDa position. The foregoing manipulations are performed according to the method as described in Chapter 12, "Antibodies; A Laboratory Manual" (Cold Spring Harbor Laboratory Press, 1988).

Example 6
Preparation of Anti-Cyclin T Antibodies (Part 2)

(1) The preparation of the antibodies was performed according to the method as described in Chapter 5, "Antibodies; A Laboratory Manual" (Cold Spring Harbor Laboratory Press, 1988), which will be described below.

A peptide comprising the amino acid sequence set forth in SEQ ID No. 5 in SEQUENCE LISTING was synthesized and conjugated to a carrier protein KLH (Keyhole Limpet Hemocyanin) by the MCS method (with the use of a heterocrosslinking agent). Thereafter, rabbits were immunized with the conjugate twice at an interval of two weeks. Five and six weeks after the initial immunization, the antibody titers raised more than 10,000-fold, at which point a large amount of antiserum was recovered and a portion thereof used in the experiment as will be described in Example 7.

Example 7
Detection of the Cyclin I Protein by Anti-cyclin I Antibody

Figure 4:
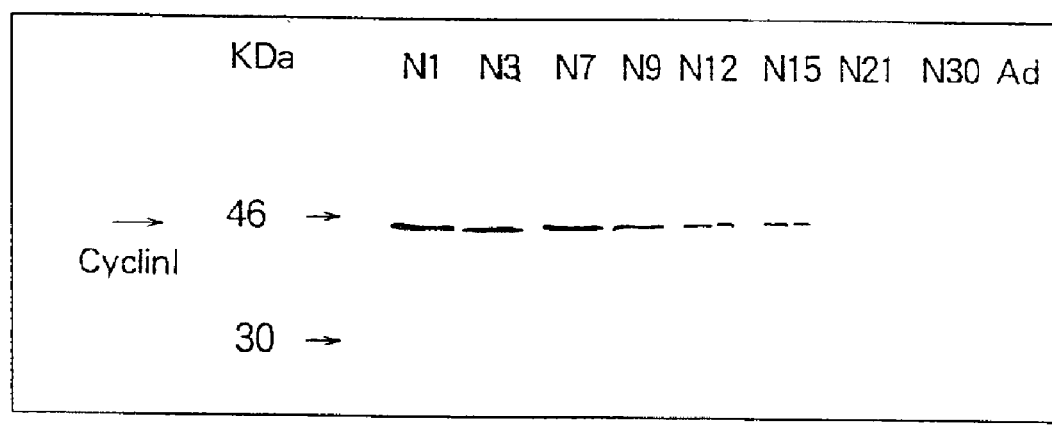
FIG. 4 shows the results of an analysis illustrative of detection of the cyclin I protein by means of an anti-cyclin I antibody according to western blotting (1, 3, 7, 9, 12, 15, 21, and 30 days old animals as denoted N1~N30, respectively; and an adult animal-3 months old as denoted Ad). The band at a 43 kDa position corresponds to the cyclin I protein having the amino acid sequence set forth in SEQ No. 1 in SEQUENCE LISTING.

According to the standard method, cell-extract solutions were prepared from the hearts of rats (1, 3, 7, 9, 12, 15, 21, 30 days old and an adult animal—3 months old), respectively. These extracted solutions were charged on acrylamide gels and subjected to analysis by western blotting using the antiserum prepared according to Example 6, which detected a band at a 43kDa position corresponding to the cyclin I protein which had the amino acid sequence set forth in SEQ No. 1 in SEQUENCE LISTING (See FIG. 4). The analysis by the western blotting method was performed according to the method as described in Chapter 12, "Antibodies; A Laboratory Manual," (Cold Spring Harbor Laboratory Press, 1988).

Example 8
Induction of Cyclin I in Colon Cancer Cells

RNAs were extracted from cancerous sections and their neighboring normal sections within excised colon cancer tissues, and analyzed by northern blotting where a fragment corresponding to bases No. 55~No. 595 of the base sequence set forth in SEQ ID No. 2 in SEQUENCE LISTING was employed as a probe. This ascertained that mRNA of the cyclin I had been induced in the cancerous sections (See FIG. 5). The northern blotting analysis was performed according to the method as described in "Cell Engineering Experimental Protocol, Shujun Publisher, pp. 149–151."

---

What is claimed is:

1. A polypeptide comprising the amino acid sequence of SEQ ID NO: 1.

* * * * *

SEQUENCE LISTING

```
<160> NUMBER OF SEQ ID NOS: 5

<210> SEQ ID NO 1
<211> LENGTH: 377
<212> TYPE: PRT
<213> ORGANISM: Homo sapiens

<400> SEQUENCE: 1

Met Lys Phe Pro Gly Pro Leu Glu Asn Gln Arg Leu Ser Phe Leu Leu
1               5                   10                  15

Glu Lys Ala Ile Thr Arg Glu Ala Gln Met Trp Lys Val Asn Val Arg
            20                  25                  30

Lys Met Pro Ser Asn Gln Asn Val Ser Pro Ser Gln Arg Asp Glu Val
        35                  40                  45

Ile Gln Trp Leu Ala Lys Leu Lys Tyr Gln Phe Asn Leu Tyr Pro Glu
    50                  55                  60

Thr Phe Ala Leu Ala Ser Ser Leu Leu Asp Arg Phe Leu Ala Thr Val
65                  70                  75                  80

Lys Ala His Pro Lys Tyr Leu Ser Cys Ile Ala Ile Ser Cys Phe Phe
                85                  90                  95

Leu Ala Ala Lys Thr Val Glu Glu Asp Glu Arg Ile Pro Val Leu Lys
            100                 105                 110

Val Leu Ala Arg Asp Ser Phe Cys Gly Cys Ser Ser Ser Glu Ile Leu
```

-continued

```
                115                 120                 125
Arg Met Glu Arg Ile Ile Leu Asp Lys Leu Asn Trp Asp Leu His Thr
    130                 135                 140
Ala Thr Pro Leu Asp Phe Leu His Ile Phe His Ala Ile Ala Val Ser
145                 150                 155                 160
Thr Arg Pro Gln Leu Leu Phe Ser Leu Pro Lys Leu Ser Pro Ser Gln
                165                 170                 175
His Leu Ala Val Leu Thr Lys Gln Leu Leu His Cys Met Ala Cys Asn
                180                 185                 190
Gln Leu Leu Gln Phe Arg Gly Ser Met Leu Ala Leu Ala Met Val Ser
                195                 200                 205
Leu Glu Met Glu Lys Leu Ile Pro Asp Trp Leu Ser Leu Thr Ile Glu
    210                 215                 220
Leu Leu Gln Lys Ala Gln Met Asp Ser Ser Gln Leu Ile His Cys Arg
225                 230                 235                 240
Glu Leu Val Ala His His Leu Ser Thr Leu Gln Ser Ser Leu Pro Leu
                245                 250                 255
Asn Ser Val Tyr Val Tyr Arg Pro Leu Lys His Thr Leu Val Thr Cys
                260                 265                 270
Asp Lys Gly Val Phe Arg Leu His Pro Ser Ser Val Pro Gly Pro Asp
    275                 280                 285
Phe Ser Lys Asp Asn Ser Lys Pro Glu Val Pro Val Arg Gly Thr Ala
    290                 295                 300
Ala Phe Tyr His His Leu Pro Ala Ala Ser Gly Cys Lys Gln Thr Ser
305                 310                 315                 320
Thr Lys Arg Lys Val Glu Glu Met Glu Val Asp Asp Phe Tyr Asp Gly
                325                 330                 335
Ile Lys Arg Leu Tyr Asn Glu Asp Asn Val Ser Glu Asn Val Gly Ser
                340                 345                 350
Val Cys Gly Thr Asp Leu Ser Arg Gln Glu Gly His Ala Ser Pro Cys
                355                 360                 365
Pro Pro Leu Gln Pro Val Ser Val Met
    370                 375

<210> SEQ ID NO 2
<211> LENGTH: 1134
<212> TYPE: DNA
<213> ORGANISM: Homo sapiens

<400> SEQUENCE: 2
atgaagtttc cagggccttt ggaaaaccag agattgtctt tcctgttgga aaaggcaatc      60
actagggaag cacagatgtg gaaagtgaat gtgcggaaaa tgccttcaaa tcagaatgtt     120
tctccatccc agagagatga agtaattcaa tggctggcca aactcaagta ccaattcaac     180
ctttacccag aaacatttgc tctggctagc agtcttttgg ataggttttt agctaccgta     240
aaggctcatc caaatactt gagttgtatt gcaatcagct gtttttttcct agctgccaag    300 actgttgagg aagatgagag aattccagta ctaaaggtat ggcaagaga cagtttctgt     360 ggatgttcct catctgaaat tttgagaatg gagagaatta ttctggataa gttgaattgg     420
gatcttcaca cagccacacc attggatttt cttcatattt tccatgccat tgcagtgtca     480
actaggcctc agttactttt cagtttgccc aaattgagcc catctcaaca tttggcagtc     540
cttaccaagc aactacttca ctgtatggcc tgcaaccaac ttctgcaatt cagaggatcc     600
atgcttgctc tggccatggt tagtctggaa atggagaaac tcattcctga ttggctttct     660
```

-continued

```
cttacaattg aactgcttca gaaagcacag atggatagct cccagttgat ccattgtcgg      720
gagcttgtgg cacatcacct ttctactctg cagtcttccc tgcctctgaa ttccgtttat      780
gtctaccgtc ccctcaagca caccctggtg acctgtgaca aaggagtgtt cagattacat      840
ccctcctctg tcccaggccc agacttctcc aaggacaaca gcaagccaga agtgccagtc      900
agaggtacag cagccttta ccatcatctc ccagctgcca gtgggtgcaa gcagacctct       960
actaaacgca aagtagagga aatggaagtg gatgacttct atgatggaat caaacggctc     1020
tataatgaag ataatgtctc agaaaatgtg ggttctgtgt gtggcactga tttatcaaga     1080
caagagggac atgcttcccc ttgtccacct ttgcagcctg tttctgtcat gtag           1134
```

<210> SEQ ID NO 3
<211> LENGTH: 33
<212> TYPE: DNA
<213> ORGANISM: Artificial Sequence
<220> FEATURE:
<223> OTHER INFORMATION: Chemically synthesized

<400> SEQUENCE: 3

```
cgttcccggg tatgaagttt ccagggcctt tgg                                    33
```

<210> SEQ ID NO 4
<211> LENGTH: 31
<212> TYPE: DNA
<213> ORGANISM: Artificial Sequence
<220> FEATURE:
<223> OTHER INFORMATION: Chemically synthesized

<400> SEQUENCE: 4

```
acggctcgag ctacatgaca gaaacaggct g                                      31
```

<210> SEQ ID NO 5
<211> LENGTH: 14
<212> TYPE: PRT
<213> ORGANISM: Artificial Sequence
<220> FEATURE:
<223> OTHER INFORMATION: Chemically synthesized

<400> SEQUENCE: 5

```
Glu Asp Asn Val Ser Glu Asn Val Gly Ser Val Cys Gly Thr
1               5                   10
```